(12) United States Patent
Attia et al.

(10) Patent No.: US 12,053,287 B2
(45) Date of Patent: Aug. 6, 2024

(54) NEURAL NETWORKS FOR ATRIAL FIBRILLATION SCREENING

(71) Applicant: Mayo Foundation for Medical Education and Research, Rochester, MN (US)

(72) Inventors: Itzhak Zachi Attia, Rochester, MN (US); Paul A. Friedman, Rochester, MN (US); Peter A. Noseworthy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 686 days.

(21) Appl. No.: 17/275,276

(22) PCT Filed: Oct. 24, 2019

(86) PCT No.: PCT/US2019/057891
§ 371 (c)(1),
(2) Date: Mar. 11, 2021

(87) PCT Pub. No.: WO2020/086865
PCT Pub. Date: Apr. 30, 2020

(65) Prior Publication Data
US 2022/0047201 A1    Feb. 17, 2022

Related U.S. Application Data

(60) Provisional application No. 62/751,395, filed on Oct. 26, 2018.

(51) Int. Cl.
| | |
|---|---|
| A61B 5/361 | (2021.01) |
| A61B 5/00 | (2006.01) |
| A61B 5/318 | (2021.01) |
| A61B 5/333 | (2021.01) |
| A61P 7/02 | (2006.01) |

(Continued)

(52) U.S. Cl.
CPC ............. *A61B 5/361* (2021.01); *A61B 5/318* (2021.01); *A61B 5/333* (2021.01); *A61B 5/7264* (2013.01); *A61P 7/02* (2018.01); *G06N 3/045* (2023.01); *G16H 20/10* (2018.01)

(58) Field of Classification Search
None
See application file for complete search history.

(56) References Cited

U.S. PATENT DOCUMENTS

| | | | | |
|---|---|---|---|---|
| 10,463,314 B1 * | 11/2019 | Najarian | ................. | G16H 50/30 |
| 10,750,968 B2 * | 8/2020 | Datta | ..................... | A61B 5/361 |
| 11,826,150 B2 * | 11/2023 | Scabellone | ............ | A61B 5/339 |

(Continued)

*Primary Examiner* — Carl H Layno
*Assistant Examiner* — Manolis Pahakis
(74) *Attorney, Agent, or Firm* — Caldwell Intellectual Property Law

(57) ABSTRACT

Systems, methods, devices, and other techniques for processing an ECG recording to assess a condition of a mammal. Assessing the condition of the mammal can include screening for atrial fibrillation, and screening for atrial fibrillation can include obtaining a first neural network input, the first neural network input representing an electrocardiogram (ECG) recording of the mammal, and processing the first neural network input with a neural network to generate an atrial fibrillation prediction for the mammal.

20 Claims, 10 Drawing Sheets

(51) Int. Cl.
     *G06N 3/045*          (2023.01)
     *G16H 20/10*         (2018.01)

(56) References Cited

U.S. PATENT DOCUMENTS

| | | | |
|---|---|---|---|
| 2008/0167567 A1* | 7/2008 | Bashour | A61B 5/352 600/521 |
| 2010/0056940 A1* | 3/2010 | Moorman | A61B 5/349 600/509 |
| 2011/0021935 A1* | 1/2011 | Ghodrati | A61B 5/024 600/519 |
| 2011/0137362 A1* | 6/2011 | Foreman | A61N 1/36114 607/9 |
| 2012/0184801 A1* | 7/2012 | Simon | A61N 1/36025 607/45 |
| 2015/0351690 A1* | 12/2015 | Toth | A61B 5/25 600/391 |
| 2016/0135702 A1* | 5/2016 | Perez | G16H 50/30 600/516 |
| 2017/0127964 A1* | 5/2017 | Moorman | A61B 5/361 |
| 2017/0156614 A1* | 6/2017 | Ibáñez Català | A61B 5/02405 |
| 2019/0038148 A1* | 2/2019 | Valys | A61B 5/7275 |
| 2019/0059763 A1* | 2/2019 | Shakur | G16H 40/67 |
| 2019/0328243 A1* | 10/2019 | Nemati | A61B 5/318 |
| 2019/0374123 A1* | 12/2019 | Bouguerra | A61B 5/7264 |
| 2019/0378617 A1* | 12/2019 | Charles | G06N 3/08 |
| 2020/0205687 A1* | 7/2020 | Rubin | A61B 5/7264 |
| 2021/0282692 A1* | 9/2021 | Yaniv | A61B 5/7267 |

* cited by examiner

| | AUC | Sensitivity | Specificity | F1 score | Accuracy |
|---|---|---|---|---|---|
| Main analysis | 0.87 (0.86-0.88) | 79.0% (77.5-80.4) | 79.5% (79.0-79.9) | 39.2% (38.1-40.3) | 79.4% (79.0-79.9) |
| Secondary analysis | 0.90 (0.90-0.91) | 87.3% (80.9-83.6) | 83.4% (83.0-83.8) | 45.4% (44.2-46.5) | 83.3% (83.0-83.7) |

Data in parentheses are 95% CIs. In the main analysis, only the score of the first normal sinus rhythm ECG in the window of interest was used. In the secondary analysis, the highest score for all ECGs done in the first month of the window of interest was used. AUC=area under the curve. ECG=electrocardiograph.

Table: Model performance

FIG. 9

NEURAL NETWORKS FOR ATRIAL FIBRILLATION SCREENING

CROSS-REFERENCE TO RELATED APPLICATIONS

This application is a National Stage application under 35 U.S.C. § 371 of International Application No. PCT/US2019/057891, having an International Filing Date of Oct. 24, 2019, which claims priority to U.S. Application Ser. No. 62/751,395, filed on Oct. 26, 2018. The disclosure of the prior application is considered part of the disclosure of this application, and is incorporated in its entirety into this application.

BACKGROUND

Cryptogenic stroke (CS) is a form of stroke or cerebral ischemia of obscure or unknown origin. The precise causes of CS remain undetermined because the CS is typically a transitory or reversible condition. It is estimated that 30-percent of strokes in the United States (approximately 200,000 cases a year) are cryptogenic.

One of the major causes of stroke is atrial fibrillation (AF) which is associated with a 5-fold risk of stroke. In patients with CS, the current AHA guidelines state, "Long term monitoring for AF may be beneficial in patients with CS and has the potential to shift the management paradigm . . . Cardiac embolism secondary to paroxysmal AF may be a common cause of assumed CS." The same guidelines argue that the detection of paroxysmal AF in post-CS patients is a priority in order to reduce the risk for recurrent events.

In recognition of this priority, post-CS patients are often provided an implantable loop recorder (ILR), which records an electrocardiogram (ECG) of the patent and alerts a physician or other healthcare provider for the presence of AF when AF is detected to have occurred in the ECG data. While the ILRs have high detection rates, the process is invasive, expensive, and generally involves a continuous monitoring infrastructure to communicate alerts to the clinicians.

SUMMARY

This specification generally describes systems, methods, devices, and other techniques for atrial fibrillation screening. A machine-learning model such as a deep neural network can be trained to process a short-recording of ECG data from a patient to generate a prediction indicating a likelihood that the patient has or will experience atrial fibrillation (e.g., paroxysmal atrial fibrillation) and/or other supraventricular tachycardia (e.g., atrial flutter, atrial tachycardia). Unlike other techniques that involve long-term or continuous monitoring (e.g., implantable loop recorders) to detect actual occurrences of atrial fibrillation, the neural networks described herein can detect a likelihood of atrial fibrillation and/or other supraventricular tachycardia (SVT) in a patient from an ECG recording that nominally represents a normal sinus rhythm. Due to structural irregularities of the heart, or the presence of other factors that can lead to atrial fibrillation, the patient's ECG in normal sinus rhythm can include features, not detectable by the human eye, but which are nonetheless highly predictive of a patient that has experienced atrial fibrillation or is susceptible to atrial fibrillation. A neural network can be trained to learn these features and predict patients that have or will experience atrial fibrillation based on ECG recordings. Moreover, because the neural network can generate atrial fibrillation predictions and/or other SVT predictions based on ECG recordings reflecting normal sinus rhythm, it is not necessary to monitor the patient for long periods of time to detect actual occurrences of atrial fibrillation and/or other SVT. Instead, a patient that has experienced cryptogenic stroke, for example, may take a brief ECG, e.g., with a 12-lead system at a healthcare provider's location or at home with a single-lead smartphone or patch system, and the neural network can process the ECG recording to determine a likelihood of atrial fibrillation and/or other SVT for the patient much more quickly. If the prediction indicates a sufficiently high likelihood of past or expected atrial fibrillation and/or other SVTs, appropriate action may be taken such as administration of medication (e.g., anticoagulants), longer term monitoring (e.g., with an implantable loop recorder) to validate the prediction, or both.

Some aspects of the subject matter disclosed herein include a method for screening for atrial fibrillation and/or other SVT (e.g., atrial flutter, atrial tachycardia). The method can include obtaining a first neural network input, where the first neural network input represents an electrocardiogram (ECG) recording of a mammal, and processing the first neural network input with a neural network to generate an atrial fibrillation prediction and/or other SVT prediction for the mammal.

These aspects and others can be implemented on a system having a data processing apparatus, e.g., which can include one or more computers in one or more locations. In some implementations, one or more computer-readable media have instructions stored thereon that, when executed by data processing apparatus, cause the data processing apparatus to perform this and other computer-based methods or processes described herein. Optionally, these aspects and others can include one or more of the following features.

The ECG recording represented by the first neural network input can describe a normal sinus rhythm for the mammal, such that the neural network generates the atrial fibrillation prediction and/or other SVT prediction for the mammal based on features of the mammal's normal sinus rhythm as indicated by the ECG recording.

The ECG recording represented by the first neural network input can span a time interval that is less than or equal to thirty seconds, fifteen seconds, ten seconds, or five seconds.

The ECG recording represented by the first neural network input can span a time interval that is less than or equal to ten minutes, five minutes, one minute, or forty-five seconds.

The mammal can be a human.

The neural network can include at least one of a feedforward portion, a convolutional portion, a recurrent portion, or a capsule portion.

The ECG recording of the mammal can include a 12-lead ECG recording.

The ECG recording of the mammal can include a single-lead ECG recording.

The ECG recording of the mammal can be based on fewer than twelve leads.

The atrial fibrillation and/or other SVT predictions can indicate a likelihood of the mammal experiencing atrial fibrillation and/or other SVT (e.g., atrial flutter, atrial tachycardia).

The atrial fibrillation prediction and/or other SVT prediction can indicate a selection of one of a plurality of possible monitoring or treatment plans.

The plurality of possible monitoring or treatment plans include a first plan to administer anticoagulants to the mammal with high likelihood of atrial fibrillation, a second plan to not administer anticoagulants, and a third plan to administer a continuous ECG for further monitoring.

The atrial fibrillation predication can indicate at least a threshold likelihood of the mammal experiencing atrial fibrillation, and the method can further include administering a treatment to lower a risk of stroke in the mammal in response to identifying that the atrial fibrillation prediction indicates at least the threshold likelihood of the mammal experiencing atrial fibrillation.

Administering the treatment can include administering an anticoagulant to the mammal.

The method can further include operations for obtaining data describing a non-ECG profile for the mammal; generating one or more second neural network inputs representing the non-ECG profile for the mammal; and processing the first neural network input along with the one or more second neural network inputs with the neural network to generate the atrial fibrillation prediction and/or other SVT prediction for the mammal.

The method can further include determining one or more morphological features of the ECG recording of the mammal; generating one or more second neural network inputs representing the one or more morphological features of the ECG recording; and processing the first neural network input along with the one or more second neural network inputs with the neural network to generate the atrial fibrillation prediction and/or other SVT prediction for the mammal.

The ECG recording of the mammal can be recorded over a first time interval, and the method can further include: obtaining a second neural network input, the second neural network input representing a second ECG recording of the mammal that was recorded over a second time interval, the first time interval and the second time interval separated by a third time interval; and processing the first neural network input along with the second neural network input with the neural network to generate the atrial fibrillation prediction and/or other SVT prediction for the mammal.

The third time interval can be at least a minute, an hour, a day, a week, or a month.

The neural network can further process, along with the first neural network input and the second neural network input, a third neural network input that indicates a length of the third time interval between the first and second time intervals when the ECG recording and the second ECG recordings were recorded, respectively.

Some aspects of the subject matter disclosed herein include a computing system having an interface and a neural network. The interface can be configured to obtain an electrocardiogram (ECG) recording of a mammal, and to generate a first neural network input representing the ECG recording. The neural network can be implemented on data processing apparatus and configured to process the first neural network input to generate an atrial fibrillation prediction and/or other SVT prediction. The system can further include at least one of a storage device for storing data representing the atrial fibrillation prediction and/or other SVT prediction, a presentation device for presenting the atrial fibrillation prediction and/or other SVT prediction, or a network interface device configured to transmit the atrial fibrillation prediction and/or other SVT prediction over a network to a provider or other interested party.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 9 depicts a table representing model performance study from the example study implementation.

DETAILED DESCRIPTION

This specification generally describes systems, methods, devices, and other techniques for atrial fibrillation screening, e.g., using neural networks or other machine-learning models. Neural networks are machine-learning models that employ multiple layers of operations to predict one or more outputs from one or more inputs. Neural networks typically include one or more hidden layers situated between an input layer and an output layer. The output of each layer is used as input to another layer in the network, e.g., the next hidden layer or the output layer. Each layer of a neural network specifies one or more transformation operations to be performed on input to the layer. Some neural network layers have operations that are referred to as neurons. Often, each neuron can receive one or more inputs and generates an output that is received by another neural network layer. The transformation operations of each layer can be carried out by one or more computers at one or more locations having installed software modules that implement the transformation operations.

Figure 1:
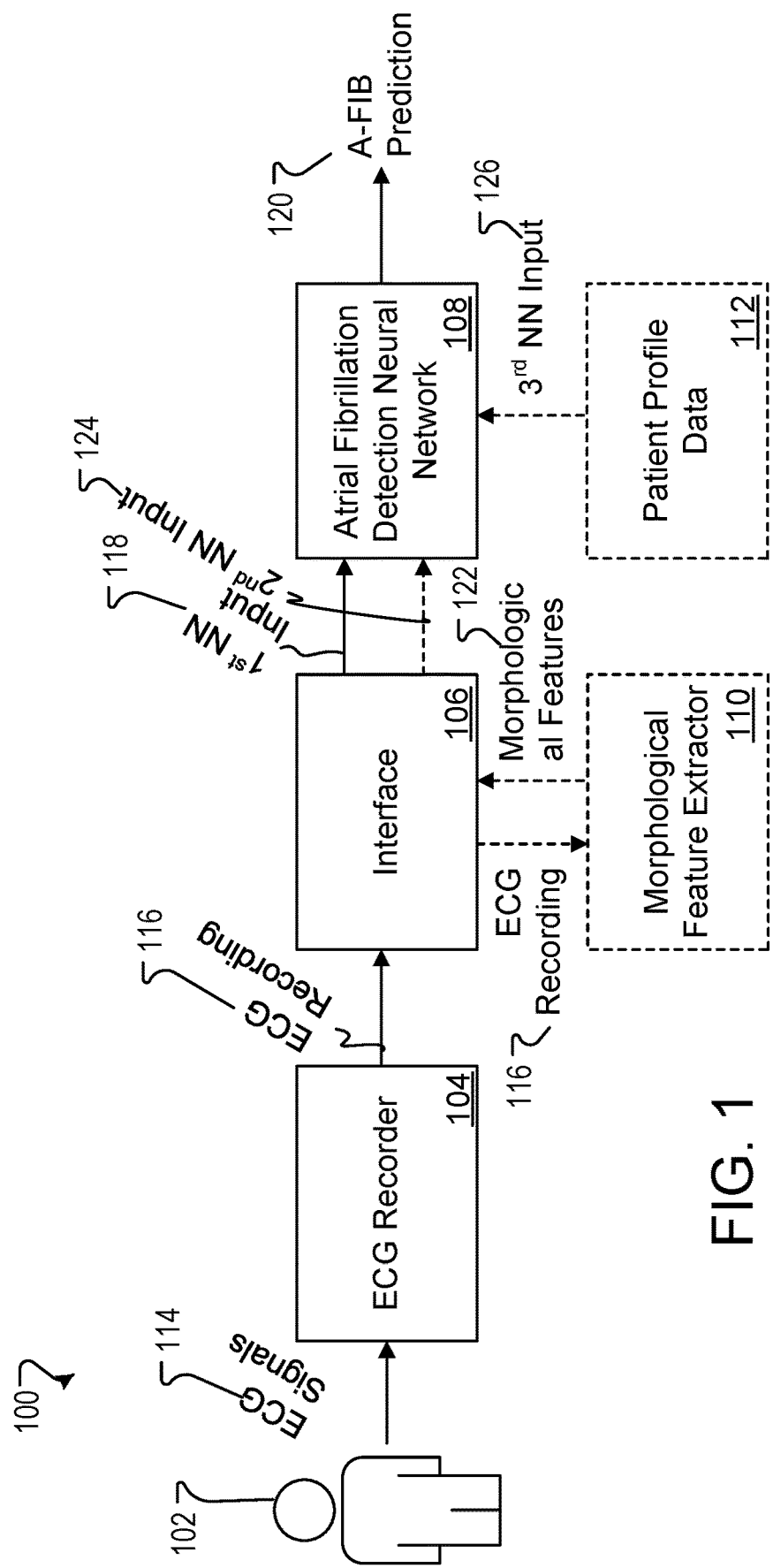
FIG. 1 is a diagram of an example system for ECG recording and atrial fibrillation screening.

Referring to FIG. 1, a diagram is shown of an example system 100 for ECG recording and atrial fibrillation screening. The system 100 is configured to record an ECG of a patient 102 and to process the recording and, optionally, additional (auxiliary) data to generate an atrial fibrillation prediction 120. The atrial fibrillation prediction 120 can indicate a likelihood that the patient 102 has experienced or is susceptible to developing atrial fibrillation. The prediction 120 can be expressed as a probability or confidence score representing a probability or confidence that the patient 102 has experienced or is susceptible to developing atrial fibrillation. In some implementations, the prediction 120 is expressed as a selection of a particular classification from multiple possible classifications that represents a most likely condition of the patient 102. For example, a binary classification can be made indicating whether there is at least a threshold probability or confidence level that the patient 102 has experienced or is susceptible to developing atrial fibrillation. The atrial fibrillation prediction 120 can identify this binary classification. As another example, the atrial fibrillation prediction 120 can indicate a recommendation or selection of a monitoring or treatment option for the patient 102 based on a likelihood of the patient 102 having experienced or being susceptible to development of atrial fibrillation. For instance, the prediction 120 can indicate a selection from the trinary of options to administer an anticoagulation medication to the patient, to not administer an anticoagulant but continue with periodic screenings, or to initiate continuous monitoring, e.g., using an implantable loop recorder ECG. Thresholds used for any decision boundaries can be extracted from retrospective analysis and can be presented with positive and negative predictive value (PPV and NPV).

The patient 102 can be a human or any other mammal for which an atrial fibrillation screening is desired. To obtain an ECG recording of the patient 102, one or more electrodes are brought into contact with a surface of the patient's body. The electrodes can be arranged according to a standard 12-lead ECG configuration, or in other known configurations. The electrodes may or may not be affixed to the patient 102. In some implementations, fewer than 12-leads are provided to for obtaining the ECG. For example, a single-lead smartphone-based ECG sensor may be employed to sense the patient's ECG based on finger contact, or a patch with an electrode array may be affixed to the patient's chest. The ECG recorder 104 includes hardware and/or software for sensing and capturing ECG signals 114 from the electrodes in contact with the patient 102. For example, the signals 114 may be filtered, amplified, and digitally sampled by recorder 104, and a recording 116 can be generated that represents the patient's ECG for each available lead over a period of time. Typically, the recording 116 may be made based on a relatively short period of measurement. For example, since a sample ECG representing the patient's normal sinus rhythm may suffice to predict the atrial fibrillation condition of the patient 102, a relatively short sample corresponding to just a few beats may be all that is required to be captured for purposes of making a prediction. In some implementations, a minimum recording time may be specified that is less than or equal to ten minutes, five minutes, one minute, forty-five seconds, thirty seconds, fifteen seconds, ten seconds, or five seconds. The ECG can be recorded while the patient 102 is in the supine position or other positions that correspond to positions of the patients whose ECGs were used as training examples for the system.

An interface 106 can be implemented on a computer or other data processing apparatus. The interface 106 receives a digitized ECG recording 116 from the ECG recorder 104 and processes the recording 116 to generate a first neural network input 118. The first neural network input 118 is a representation of the ECG recording that is suitable for processing by the atrial fibrillation detection neural network 108. The first neural network input 118, for example, can identify values of the ECG signal level for each lead over the full recording time or over a subset of the recording time (e.g., a time interval that corresponds to a single heartbeat). The first neural network input 118 can represent the ECG recording for one or more individual beats or can represent an averaged beat based on ECG recordings from several measured beats.

The atrial fibrillation detection neural network 108 is configured to process the first neural network input 118 and to generate atrial fibrillation prediction 120 based on the first neural network input 118. The neural network 108 can include multiple layers of operations that have been trained to discern an atrial fibrillation condition of a patient based on ECG recordings of a patient's normal sinus rhythm. The neural network 108 can be a feedforward neural network, a recurrent neural network, a convolutional neural network, a capsule network, or may include various portions having different characteristics, such as feedforward layers, recurrent layers, and/or convolutional layers. The atrial fibrillation detection neural network 108 can be implemented on one or more computers or other data processing apparatus in one or more locations. The network 108 may be implemented on a smartphone or other personal device (e.g., tablet, desktop or notebook computer) in the same location as the patient 102, or may be implemented on one or more remote servers in communication with the interface 106.

Figure 5:
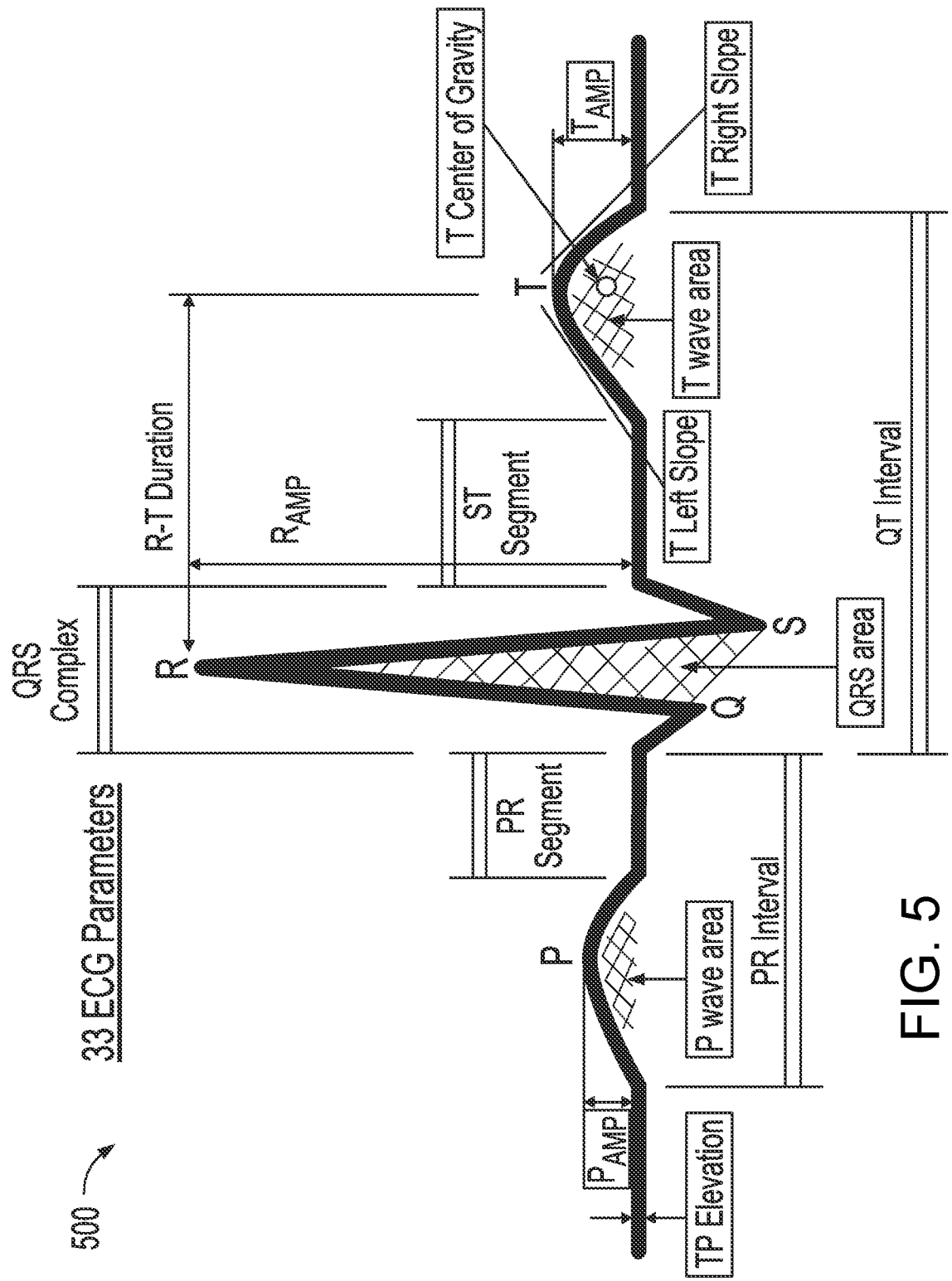
FIG. 5 is an example diagram of a segment of an ECG recording for a patient.

In some implementations, the atrial fibrillation detection neural network 108 is configured to process additional (auxiliary) information in generating atrial fibrillation prediction 120. For example, the network 108 may process a second neural network input 124 in addition to the first neural network input 118 to generate the atrial fibrillation prediction 120. The second neural network input 124 represents morphological features of the patient's ECG. FIG. 5, for instance, depicts a waveform or tracing 500 for a single beat from a patient's ECG. The waveform includes several segments including a P-wave, a QRS-complex, and a T-wave. The interface 106 can provide the ECG recording 116 to a morphological feature extractor 110 for analysis, and the extractor 110 can measure various morphological features of one or more beats (or a composite or averaged beat) from the ECG recording 116. The morphological features are parameters that describe attributes of the shape of the beat, including attributes of individual segments of the beat and attributes between segments. A number of morphological features that may be employed for atrial fibrillation prediction are labeled in FIG. 5, such as a duration of the QRS-complex, am amplitude of the P-wave, R-wave, or T-wave, an area of the P-wave, QRS-complex, or T-wave, slopes of any of the waves, distances between the waves, and centers-of-gravity of the waves. The morphological feature extractor 110 provides values for the morphological features 122 to the interface 106, and the interface 106 formats them into an acceptable form for processing by atrial fibrillation detection neural network 108 as second neural network input 124. The atrial fibrillation detection neural network 108 processes the first and second inputs 118, 124 to generate the atrial fibrillation prediction 120.

In some implementations, the neural network 108 processes one or more third neural network inputs 126 representing patient profile data from a database 112. The patient profile data is another form of auxiliary information, and in particular it indicates non-ECG descriptions of the patient 102. For example, the third neural network inputs 126 representing patient profile data can include indications of one or more of age, weight, or sex of the patient 102, and/or other attributes of the patient 102. The atrial fibrillation detection neural network 108 can process the first neural network input 118 and none, one, or both of second neural network input 124 and third neural network input 126 to generate atrial fibrillation prediction 120.

Figure 2:
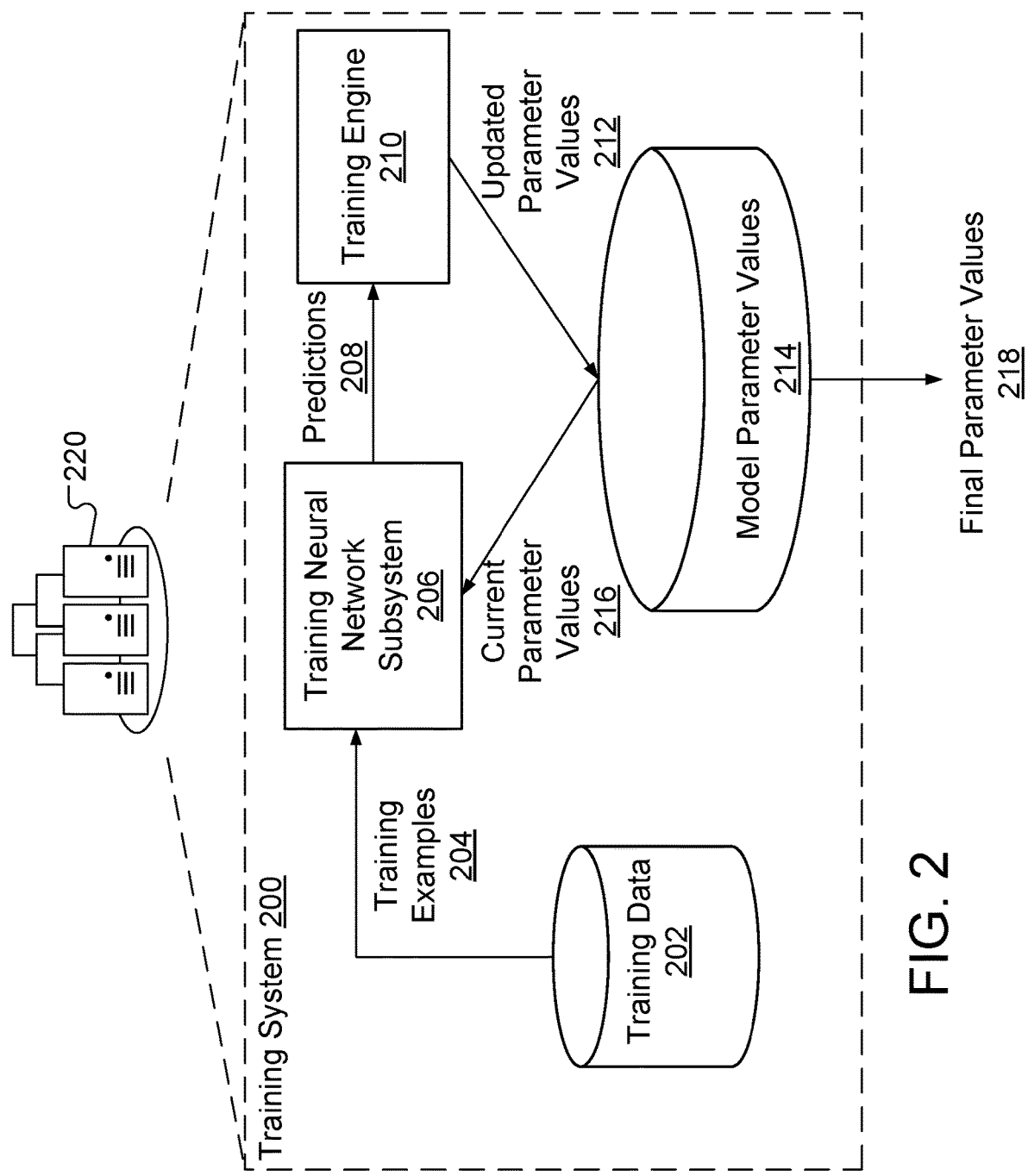
FIG. 2 depicts an example system for training an atrial fibrillation detection neural network.

FIG. 2 depicts an example system 200 for training an atrial fibrillation detection neural network. The training system 200 can be hosted within a data center 112, which can be a distributed computing system having hundreds or thousands of computers in one or more locations.

The training system 200 includes a training neural network subsystem 206 that can implement the operations of each layer of a neural network that is designed to make atrial fibrillation predictions from ECG recordings and, optionally, auxiliary information such as morphological features and patient profile data. The training neural network subsystem 206 includes a plurality of computing devices having software or hardware modules that implement the respective operations of each layer of the neural network according to an architecture of the neural network. Generally, the training neural network subsystem 206 has the same architecture as the atrial fibrillation detection neural network 108. However, the training system 200 need not use the same hardware to compute the operations of each layer. In other words, the training system 200 can use CPUs only, highly parallelized hardware, or some combination of these.

The training neural network subsystem 206 can compute the operations of each layer of the training neural network subsystem 206 (or atrial fibrillation detection neural network 108) using current parameter values 216 stored in a collection of model parameter values 214. Although illustrated as being logically separated, the model parameter values 214 and the software or hardware modules performing the operations may actually be located on the same computing device or on the same memory device.

The training neural network subsystem 206 can generate, for each training example 204, an atrial fibrillation prediction 208. A training engine 210 analyzes the predictions 208 and compares the predictions 208 to labels in the training examples 204 that indicate target predictions for each training example 204. The training engine 210 then generates updated model parameter values 214 by using an appropriate updating technique, e.g., stochastic gradient descent with backpropagation. The training engine 210 can then update the collection of model parameter values 214 using the updated model parameter values 212. For example, each training example 204 can include a first component representing a single- or multi-lead ECG recording of a patient and a label indicating a target atrial fibrillation prediction. The first component can represent an ECG of a patient under normal sinus rhythm, and the label can indicate whether that particular patient is known to have actually experienced atrial fibrillation at another time. In this way, the neural network 108 can be trained using sinus rhythm ECGs obtained in patients known and validated atrial fibrillation versus patients with no known atrial fibrillation. The training examples can also include additional components representing morphological features or patient profile data, for example.

After training is complete, the training system 200 can provide a final set of parameter values 218 to the system 100 for use in making atrial fibrillation predictions 120. The training system 200 can provide the final set of model parameter values 218 by a wired or wireless connection to the system 100 and neural network 108, for example.

Figure 3:
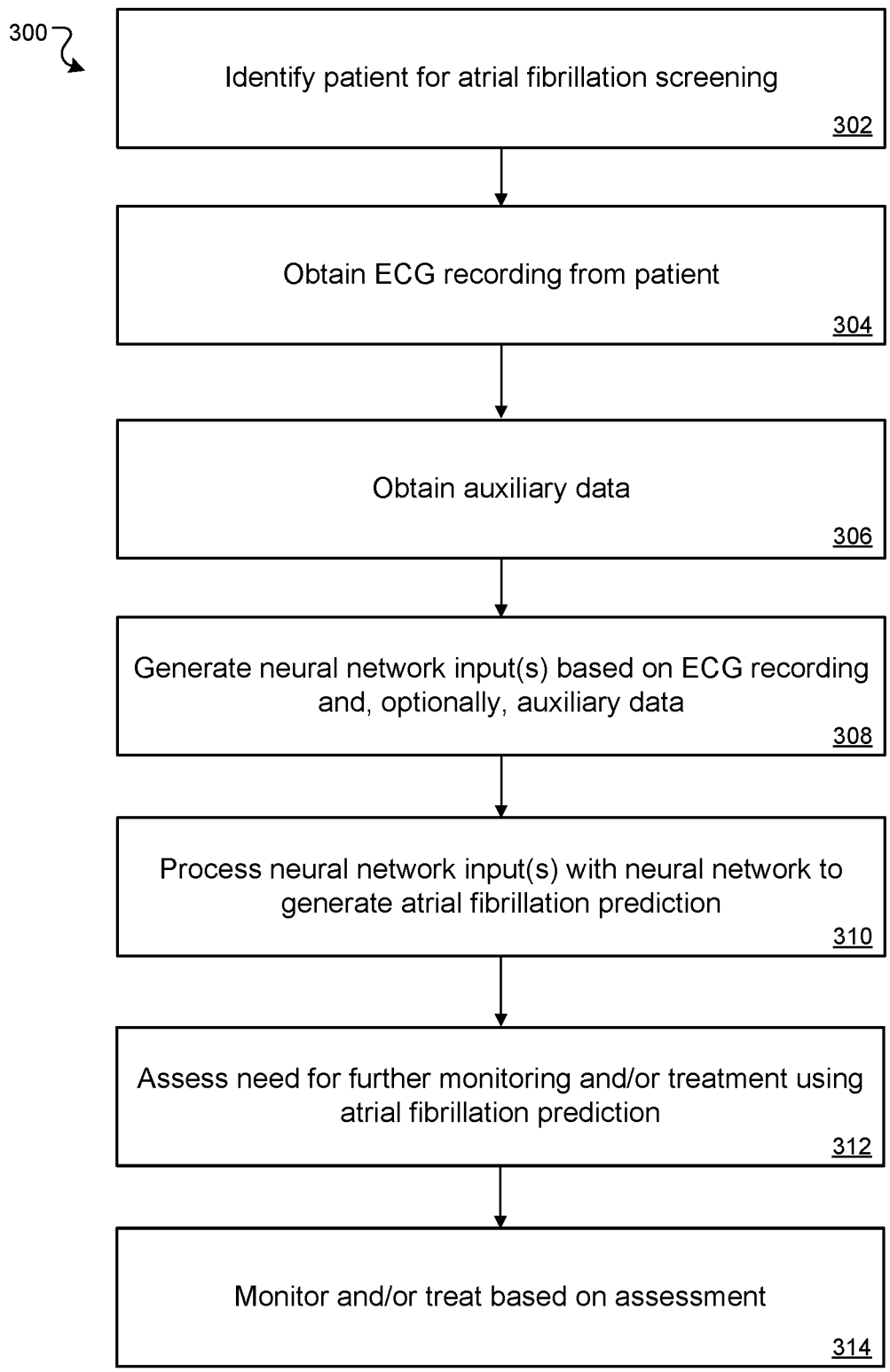
FIG. 3 is a flowchart of an example process for recording an ECG of a patient and processing data representative of the recording to generate an atrial fibrillation prediction. The atrial fibrillation prediction can be used by a physician or other human or automated decision-maker to determine or recommend a monitoring and/or treatment regime for the patient.

FIG. 3 is a flowchart of an example process 300 for recording an ECG of a patient and processing data representative of the recording to generate an atrial fibrillation prediction. The atrial fibrillation prediction can be used by a physician or other human or automated decision-maker to determine or recommend a monitoring and/or treatment regime for the patient. A patient is identified for atrial fibrillation screening, e.g., due to the patient having suffered a cryptogenic stroke (302). An ECG recording is obtained from the patient (304). The ECG recording may be obtained using a single-lead or multi-lead (e.g., standard 12-lead) ECG. Optionally, auxiliary data such as morphological features for the ECG and/or patient profile data can be obtained (306). The system generates neural network inputs based on the ECG recording and the auxiliary data, if available (308). The atrial fibrillation detection neural network processes the neural network inputs to generate the atrial fibrillation prediction (310). A physician or other healthcare provider can assess the need for further monitoring or treatment of the patient's condition based on the atrial fibrillation prediction (312). For example, to lower the risk of stroke once the patient has been identified as likely having atrial fibrillation, medication such as anticoagulants may be prescribed to the patient. Additionally, the patient may undergo longer-term continuous monitoring to identify actual episodes of atrial fibrillation, e.g., using an implantable loop recorder (314).

Figure 4:
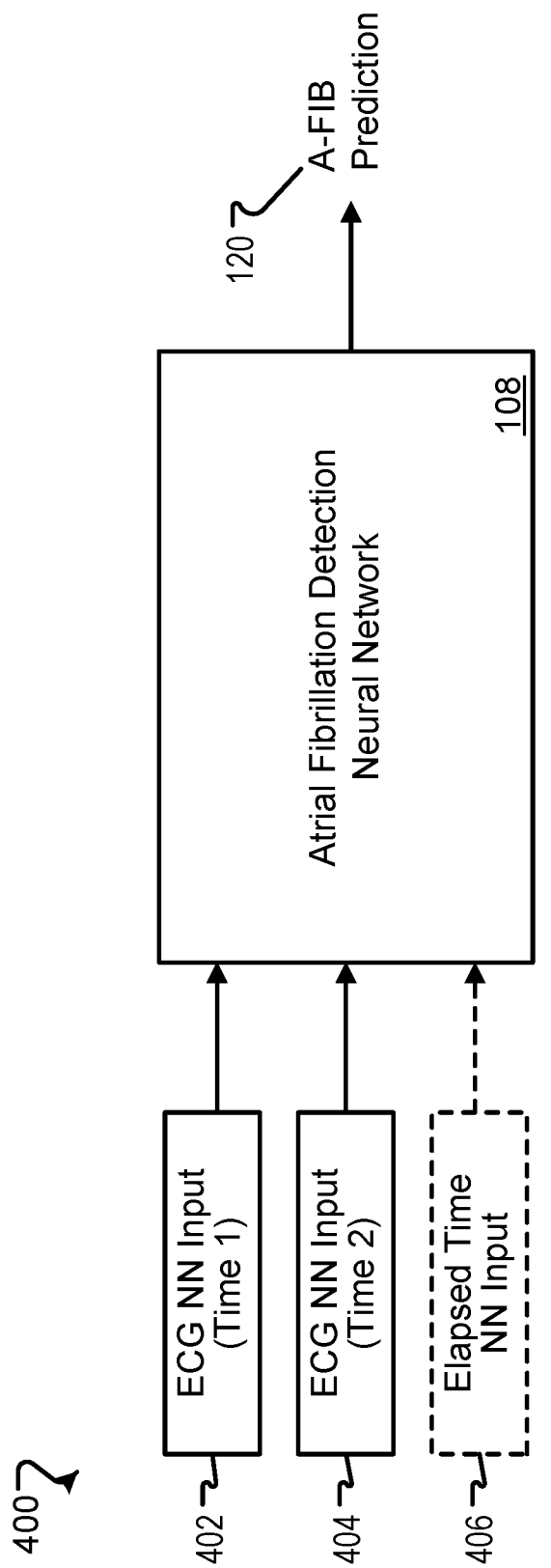
FIG. 4 is a diagram of an example neural network that processes temporally spaced ECG recordings of a patient to generate an atrial fibrillation prediction for the patient based in part on features representing differences between the ECG recordings over time.

FIG. 4 is a diagram of an example neural network system 400 that processes temporally spaced ECG recordings of a patient to generate an atrial fibrillation prediction for the patient based in part on features representing differences between the ECG recordings over time. Here, the atrial fibrillation detection neural network 108 is configured to process a first neural network input 402 representing an ECG recording (e.g., under normal sinus rhythm) of the patient at a first time (e.g., over a short time interval such as less than or equal to 30, 20, 15, 10, or 5 seconds) and a second neural network input 404 representing a second ECG recording (e.g., under normal sinus rhythm) of the patient at a second time (e.g., over a short time interval such as less than or equal to 30, 20, 15, 10, or 5 seconds). In some cases, the neural network 108 further processes a neural network input 406 that indicates an amount of elapsed time between the times the first and second ECG recordings representing in inputs 402 and 404 were recorded. For example, the input 406 can indicate that the ECG recordings were taken a number of hours, days, weeks, months, or years apart from each other. The neural network 108 can then process each of the inputs 402, 404, and 406 to generate an atrial fibrillation prediction 120.

Example Implementation Study

This example describes the results of a study in which an artificial intelligence (AI)-model including a convolutional neural network was developed and tested to detect the electrocardiographic signature of atrial fibrillation present during normal sinus rhythm. The model was developed to process an ECG signature for a patient using a standard 10-second, 12-lead ECG recording. The example implementation was trained based on ECGs acquired from a set of patients aged 18 years or older having at least one digital, normal sinus rhythm, standard 10-second, 12-lead ECG acquired in the supine position at the MAYO CLINIC ECG laboratory between Dec. 31, 1993, and Jul. 21, 2017, with rhythm labels validated by trained personnel under cardiologist supervision. ECG samples were assigned binary classification labels indicating either (1) positive for atrial fibrillation or (2) negative for no atrial fibrillation. ECG samples that demonstrated atrial fibrillation were classified as positive for atrial fibrillation. Further, various ECG samples were allocated to either the training, internal validation, or testing datasets in a 7:1:2 ratio. The area under the curve (AUC) of the receiver operating characteristic curve was calculated for the internal validation dataset to select a probability threshold, which was applied to the testing dataset. Model performance was evaluated on the testing dataset by calculating the AUC and the accuracy, sensitivity, specificity, and F1 score with two-sided 95% confidence intervals (CIs).

The study included ECGs from 180,922 patients, which provided 649,931 normal sinus rhythm ECG samples for analysis: 454,789 ECGs recorded from 126,526 patients in the training dataset, 64,340 ECGs from 18,116 patients in the internal validation dataset, and 130,802 ECGs from 36,280 patients in the testing dataset. 3,051 (8.4%) patients in the testing dataset had verified atrial fibrillation before the normal sinus rhythm ECG tested by the model. The example implementation of the neural network system identified atrial fibrillation with an AUC of 0.87 (95% CI 0.86-0.88), sensitivity of 79.0% (77.5-80.4), specificity of 79.5% (79.0-79.9), F1 score of 39.2% (38.1-40.3), and overall accuracy of 79.4% (79.0-79.9). Including all ECGs acquired during the first month of each patient's window of interest (i.e., the study start date or 31 days before the first recorded atrial fibrillation ECG) increased the AUC to 0.90 (0.90-0.91), sensitivity to 82.3% (80.9-83.6), specificity to 83.4% (83.0-83.8), F1 score to 45.4% (44.2-46.5), and overall accuracy to 83.3% (83.0-83.7).

Data Sources and Study Population. The study included all patients aged 18 years or older with at least one digital, normal sinus rhythm, standard 10-second, 12-lead ECG acquired in the supine position at the MAYO CLINIC ECG laboratory between Dec. 31, 1993, and Jul. 21, 2017. All ECGs were acquired at a sampling rate of 500 Hz using a GE-MARQUETTE ECG machine (Marquette, WI, USA) and the raw data were stored using the MUSE data management system. ECGs are initially read by the GE-MARQUETTE ECG system and then over-read by a physician-supervised, trained technician, with corrections made to the diagnostic labels as needed. For the purposes of the present study, any ECG with a rhythm of atrial fibrillation or atrial flutter was classified as having atrial fibrillation. This classification was chosen because guidelines recommend anticoagulation in the presence of either atrial fibrillation or atrial flutter and both rhythms often coexist.

Identifying Study Groups. Patients were classified into two groups: patients positive for atrial fibrillation, who had at least one atrial fibrillation rhythm recorded on a MAYO CLINIC ECG, and patients negative for atrial fibrillation, who had no ECGs with atrial fibrillation recorded and additionally had no reference to atrial fibrillation in the diagnostic codes in their electronic medical record. Patients with a diagnosis code for atrial fibrillation but no ECG documentation of atrial fibrillation were considered to have unverified atrial fibrillation and were excluded from the analysis to avoid ambiguity. ECGs with paced rhythms were also excluded.

Figure 6:
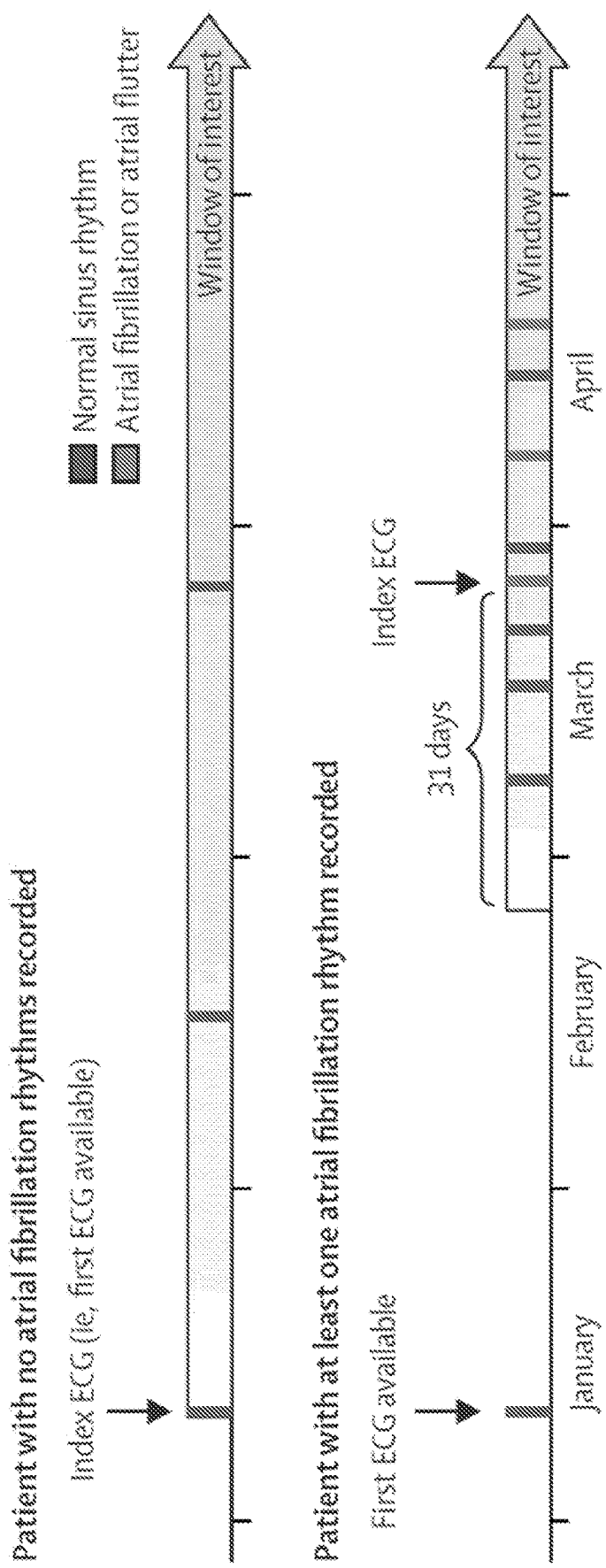
FIG. 6 is an illustration showing an example ECG selection for two patients with multiple ECGs over the same year. The example study implementation used all normal sinus rhythm ECGs for patients with no ECGs with atrial fibrillation recorded and the window of interest began on the date of their first ECG. For patients with at least one atrial fibrillation rhythm recorded, the first ECG recording atrial fibrillation or atrial flutter was the index ECG and the window of interest began 31 days before the index ECG. For all patients, the window of interest extended until the study ended.

ECG Selection For Patients With Multiple ECGs. Many study patients had multiple ECGs recorded over the inclusion period. The study defined a window of interest for each patient for the purpose of analysis (FIG. 6). For patients who had had at least one atrial fibrillation rhythm recorded, the first recorded atrial fibrillation ECG was defined as the index ECG and the first day of the window of interest was defined as 31 days before the date of the index ECG. This window of interest was chosen with the assumption that the structural changes associated with atrial fibrillation would be present before the first recorded atrial fibrillation episode; a relatively short time interval was chosen as a conservative measure to avoid using ECGs before any structural changes developed. For patients with no ECGs with atrial fibrillation recorded, the index ECG was defined as the date of the first ECG available for that patient in the MAYO CLINIC Digital Data Vault. During training, all the ECGs in the window of interest were used to allow the network to have more samples; for the testing and validation sets, only the first normal sinus rhythm ECG within the window of interest was used to avoid repeated measurements and to mimic a real screening scenario.

Outcomes. The primary outcome of the study was the development of an AI model (e.g., a system implementing a trained convolutional neural network) capable of identifying patients with atrial fibrillation based on an input representing a standard 10-second, 12-lead ECG recorded during sinus rhythm. This performance was mathematically assessed by the area under the curve (AUC) of the receiver operating characteristic (ROC) curve, as well as the sensitivity, specificity, accuracy, and F1 score of the model. A secondary analysis was performed to determine whether use of more than one sinus rhythm ECG per patient improved the AUC of the AI-enabled ECG for the detection of a history of atrial fibrillation. A secondary analysis included only the first normal sinus rhythm after the index atrial fibrillation ECG.

Overview Of The AI Model. The AI model that is the subject of the present study implemented a convolutional neural network (CNN) using the KERAS FRAMEWORK with a TENSORFLOW (GOOGLE; Mountain View, CA, USA) backend and PYTHON. The 12-lead ECG was recorded using eight physical leads and four augmented leads created as a linear function of leads I and II, which do not contain incremental information. To optimize performance, only the eight independent leads (leads I, II, and V1-6) were selected because any linear function of the leads could be learned by the models. This reduced the original 12×5000 matrix (i.e., 12 leads by 10-second duration sampled at 500 Hz) to an 8×5000 matrix. The long axis (5000) represents the temporal axis and most of the convolutions were used on it to allow the model to extract morphological and temporal features, while the short axis (8) represents the lead or spatial axis and was only used on layer to fuse the data from all the leads. The network was composed of ten residual blocks, which allowed the signals to feed directly to the next layer in addition to the processing performed in the current layer; this allowed the network to learn even when using a very large number of layers. Each residual block was implemented using two blocks, each composed of a batch-normalization layer that accounts for normalization of the data distribution; a non-linear ReLU activation function with output zero for negative inputs and identity output for positive inputs, the non-linearity of which allows the network to create a complex non-linear representation of the ECGs for automatic feature extraction; and a convolution layer. The residual blocks were completed with a shortcut link to allow gradient propagation implemented using a 1×1 convolution layer between the input of the residual block to its output and finally a max pooling layer. The nine different residual blocks had access to a single lead and the last convolution layer fused all eight independent leads using a 1×8 convolutional layer. Following the last convolutional layer, the data were fed to a dropout layer and to the final output layer that was activated using the softmax function, which generated a probability of atrial fibrillation. The model was trained on a computer with 224 GB ram and four K-80 (NVIDIA) graphics processing units (GPUs) that were used to train the model in parallel using the KERAS single machine-multi GPU parallelism.

All patients and their digitally available MAYO CLINIC ECGs included in the cohort were randomly assigned in a 7:1:2 ratio to one of three groups: training, internal validation, and testing datasets. The training dataset contained ECGs from 70% of the patient cohort and was used to train the network; the internal validation dataset with ECGs from 10% of the cohort was used to optimize the network and select the network hyper-parameters; and the testing dataset, including ECGs from the remaining 20% of patients who were not in the training or validation datasets, was used to assess the AI-enabled ECGs' ability to detect a history of atrial fibrillation. A ROC curve was created for the testing and validation datasets to assess the AUC of the AI-enabled ECG acquired during normal sinus rhythm to determine whether atrial fibrillation was present. Using the ROC curve for the small internal validation set, a probability threshold was selected and applied the same threshold to the testing dataset for derivation of the testing dataset accuracy, sensitivity, specificity, and F1 score.

Statistical Analysis. Statistical optimization of the CNN was done through iterative training using the KERAS package. Once a final fitted model was obtained, the diagnostic performance was more formally analyzed. Measures of diagnostic performance included the ROC AUC, accuracy (ie, a weighted average of sensitivity and specifcity indicating the percentage of patients whose labels were predicted correctly), sensitivity, specificity, and the F1 score (i.e., the harmonic mean of the sensitivity and positive predictive value). Two-sided 95% confidence intervals (CIs) were used to summarize the sample variability in the estimates. Exact (Clopper-Pearson) CIs were employed to be conservative for accuracy, sensitivity, and specificity. The CI for the AUC was estimated using the Sun and Su optimization of the Delong method using the pROC package whereas the CI for F1 was obtained using the bootstrap method with 2,000 replications. All analyses were performed using R, version 3.4.2.

Figure 7:
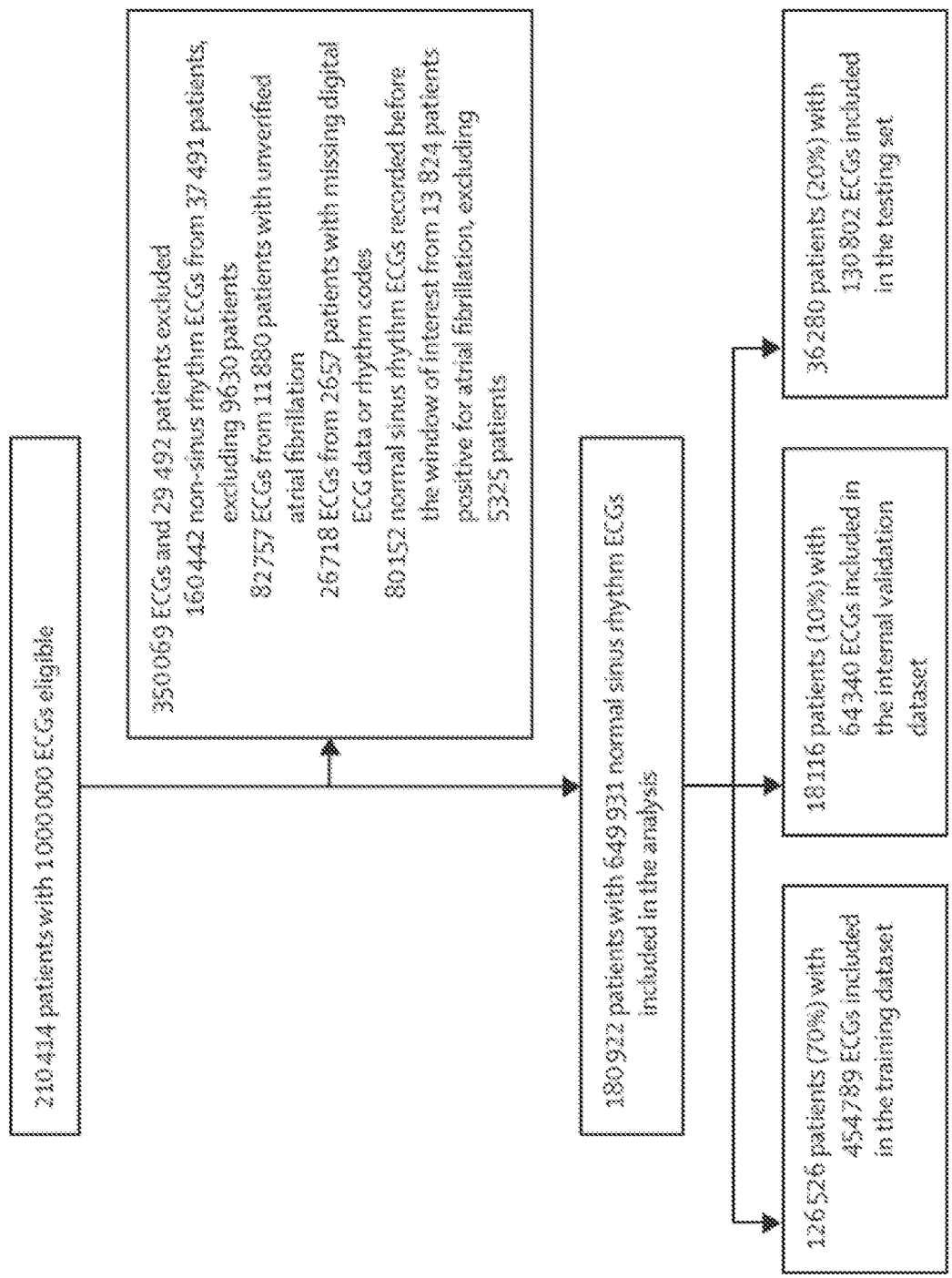
FIG. 7 is a patient flow diagram.

Results. The study identified 210,414 patients with 1,000,000 ECGs and, after applying exclusion criteria, included 180,922 patients with 649,931 normal sinus rhythm ECGs for analysis (FIG. 7). The model was trained model using 454,789 ECGs recorded from 126,526 patients, with a mean of 3-6 ECGs (standard deviation 4.8) per patient. In patients with at least one atrial fibrillation recorded in the testing dataset, 1,698 (55.7%) of the 3,051 first normal sinus rhythm ECGs in the window of interest were within 1 week of the index atrial fibrillation ECG (median number of days between ECGs 0, IQR −4 to 24). Among all included patients, the mean age was 60.3 years (standard deviation 16.5) on the date of the index ECG, 89,791 (49.6%) patients were men, and 15,419 (8.5%) had at least one recorded atrial fibrillation. In the internal validation set, there were 64,340 ECGs from 18,116 patients with a mean of 3.6 ECGs (standard deviation 4.8) per patient. Patients had a mean age of 60.3 years (standard deviation 16.7) at their first visit, 8,983 (49.6%) were men, and 1,573 (8.7%) had at least one recorded atrial fibrillation. In the testing dataset, there were 130802 ECGs from 36280 patients with a mean of 3.6 ECGs (4.9) per patient. Patients had a mean age of 60.1 years (16.8) at their first visit, 18,068 (49.8%) were men, and 3,051 (8.4%) had at least one recorded atrial fibrillation.

Figure 8:
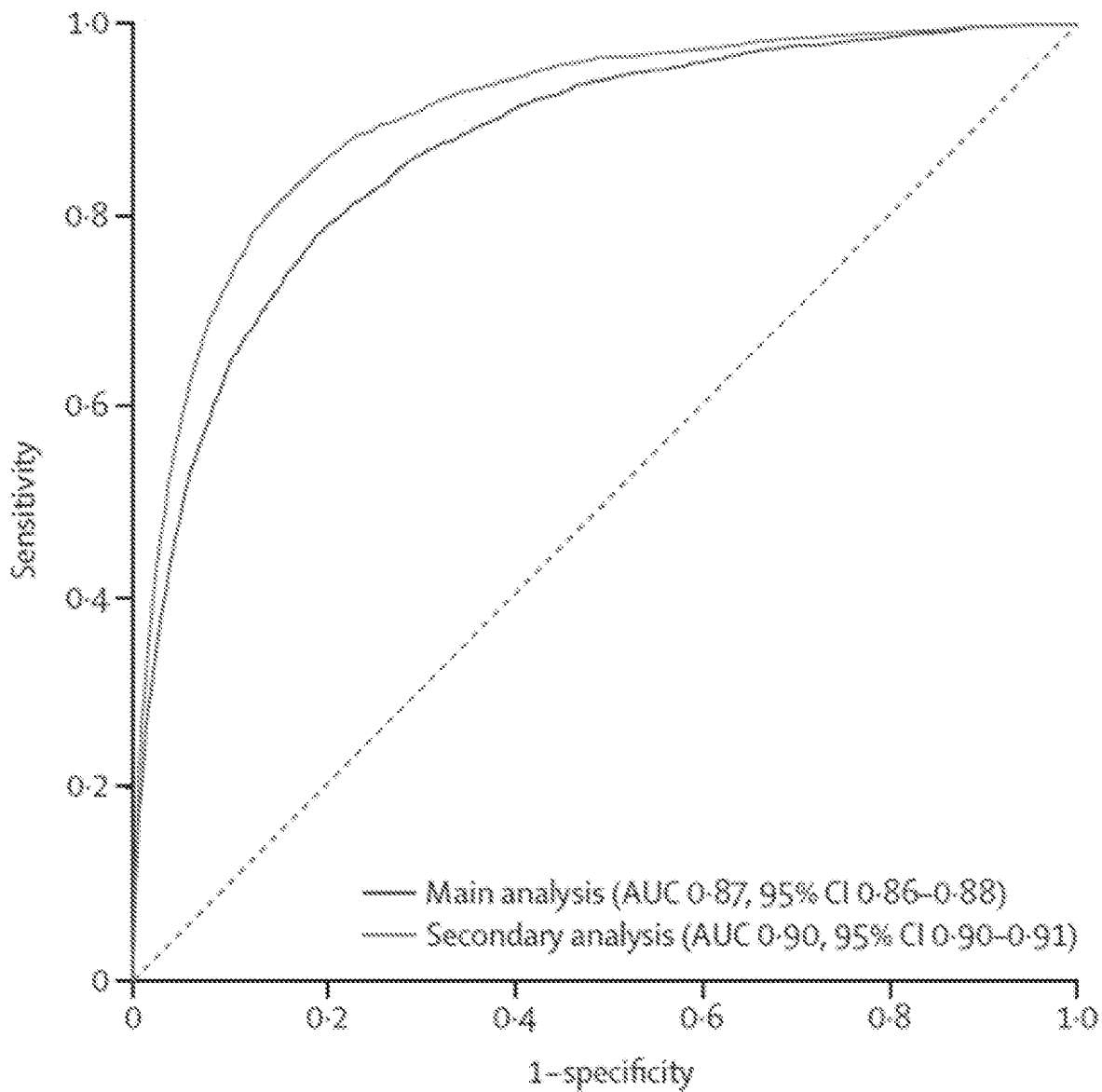
FIG. 8 is a plot of ROC curves for the convolutional neural networks on the testing dataset. In the main analysis, only the score of the first normal sinus rhythm ECG in the window of interest was used. In the secondary analysis, the highest score for all ECGs done in the first month of the window of interest was used.

When testing the model on the first sinus rhythm ECG for each patient, the ROC AUC for the detection of atrial fibrillation was 0.87 (0.86-0.88) using the internal validation set and 0.87 (0.86-0.88) using the testing dataset (FIG. 9). The probability value that yielded similar sensitivity, specificity, and accuracy of 79.2% on the internal validation set was applied to the testing set and yielded an F1 score of 39.2% (95% CI 38.1-40.3), sensitivity of 79.0% (77.5-80.4), specificity of 79.5% (79.0-79.9), and an overall accuracy of 79.4% (79.0-79.9; table). The effect of using multiple sinus rhythm ECGs from the same patient was also tested, as the additional data seemed likely to improve the network performance of AI-enabled ECG. Multiple ECGs provide the model with more information about each patient and can mask outliers. When testing the model on all of the sinus rhythm ECGs in the first 31 days from the study start date and selecting the average and maximum probability of atrial fibrillation scores, the AUC improved to 0.89 (0.89-0.90) using the average score on the test dataset and to 0.90 (0.90-0.91) when applying a more sensitive approach of using the score of the ECG with the highest risk (FIGS. 8-9). Similar improvements were found when doing the same analysis on the internal validation set: the AUC improved to 0.89 (0.89-0.90) using the average score and to 0.90 (0.89-0.91) when applying a more sensitive approach of using the score of the ECG with the highest risk. In another secondary analysis on the testing dataset, only the first normal sinus rhythm after the onset of atrial fibrillation was included, and the AUC of the network improved to 0.90 (0.89-0.91). As in the primary analysis, we found the probability threshold that yielded a similar sensitivity and specificity on the internal validation set and used that to classify the patients in the testing dataset. When using the maximum score with the calculated threshold, the F1 score improved to 45.4% (95% CI 44.2-46.5), sensitivity improved to 82.3% (80.9-83.6), and specificity improved to 83.4% (83.0-83.8) with an overall accuracy of 83.3% (83.0-83.7) on the testing dataset.

Figure 10:
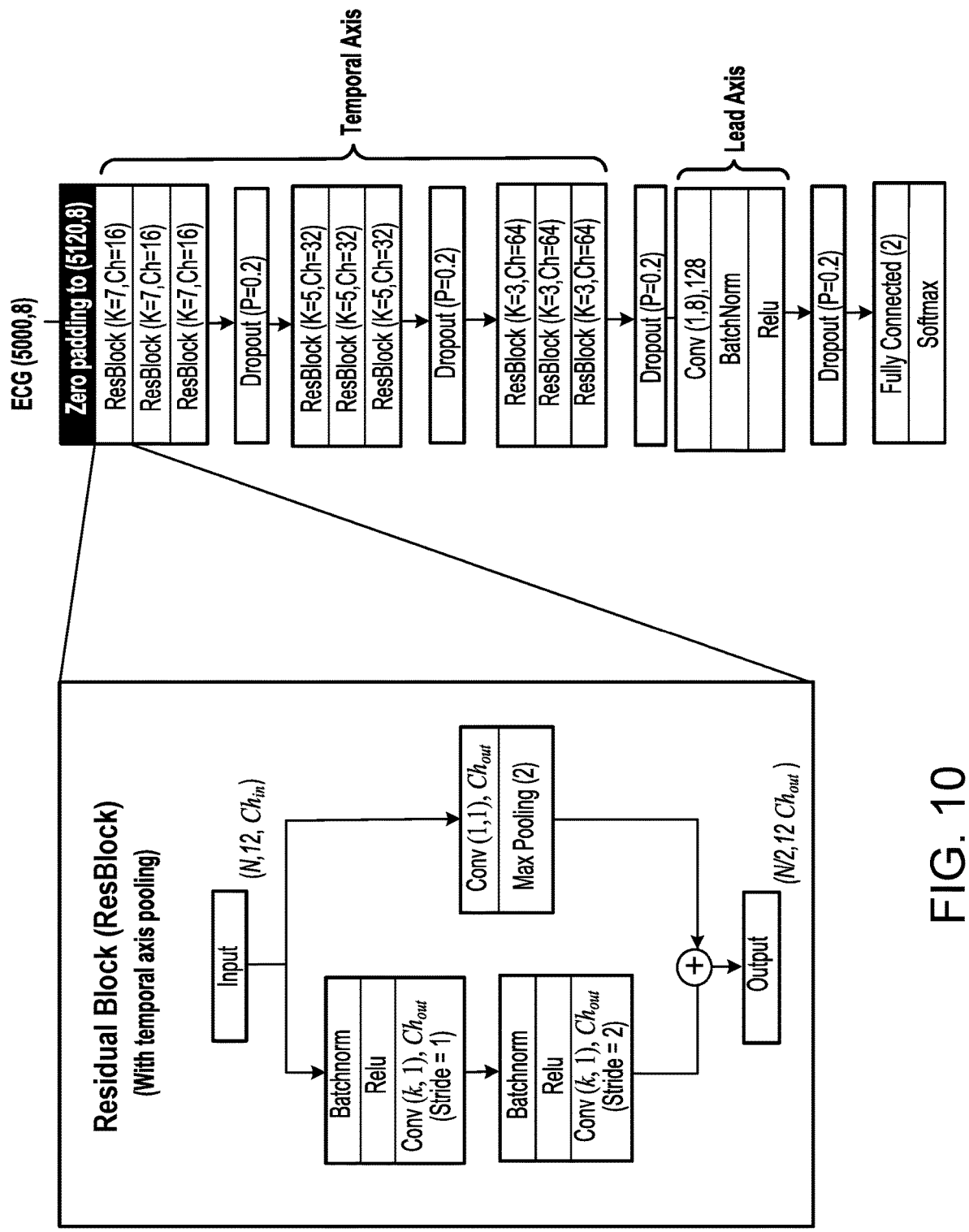
FIG. 10 depicts the architecture of an example neural network configured to process inputs representing a recording of a patient's ECG during normal sinus rhythm to generate an output representing a likelihood of the patient having or developing atrial fibrillation.

Architecture. FIG. 10 depicts the architecture of an example neural network consistent with the model employed in this study configured to process inputs representing a recording of a patient's ECG during normal sinus rhythm to generate an output representing a likelihood of the patient having or developing atrial fibrillation. The network employs a collection of layers structured in a repetitive way. Residual blocks are made of group of layers in a particular order that allows the information to flow in parallel, in one arm, six layers of batch normalization, non-linear activation and convolutional layers are used for feature extraction, and on the other arm, the data flows direction (downsampling by a factor of two to match the output size of the first arm). Residual blocks allow the network to be deep as the gradients can flow through the skip link, after each tree Resblock, a dropout layer is used to randomly mask 20% of the data for each training step. This practice is used to reduce overfitting and acts as a regulizer, preventing the network from using only small groups of features (as sometime the important features are masked, the network is forced to learn other features). After the 9 residual blocks, a convolutional layer is used to combine the features from the various leads. Batch normalization blocks are used across the model to reduce covariates shift and normalizes the data. The "ReLU" activation function and the "max pooling" functions are used in this example to allow the model to represent non-linear functions learn more complex features. They can also create a certain buffer between the different layers to prevent the model from collapsing into a shallow linear model. The use of max pooling can also help to reduce temporal resolution as more features are learned.

Discussion. Implementations of the AI model (i.e., the model including the aforementioned convolutional neural network) developed and tested through this study can, in certain cases, provide various advantages. In some examples, the model can be used to identify/screen for undetected atrial fibrillation with an inexpensive, widely available, point-of-care test. For instance, once the model is trained, it can be implemented on a typical consumer device (e.g., a smartphone, smartwatch or other wearable device, tablet, laptop, or personal desktop computer) and configured to process standard digital 12-lead ECG recordings. The model can thus facilitate point-of-care diagnosis by allowing application of the algorithm on low-cost, widely available technologies. For example, other implementations of the model may process inputs representing ECGs having signals from just a single lead or another number of leads fewer than the 12-lead standard. Additionally, the recording period for the input may be shorter or longer than the 10-seconds used in this study.

It is noted that the threshold for a positive result (i.e., a positive classification of atrial fibrillation) could be altered to suit the purposes of different clinical applications. The current binary cutoff was chosen to balance sensitivity and specificity, but a more sensitive cutoff point might be useful in excluding patients who do not need monitoring of atrial fibrillation after stroke or a more specific cutoff point could be used for screening of otherwise healthy people with a low pretest probability of atrial fibrillation, for instance.

Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, which is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, off-the-shelf or custom-made parallel processing subsystems, e.g., a GPU or another kind of special-purpose processing subsystem. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a sub combination.

What is claimed is:

1. A method for screening for atrial fibrillation, the method comprising:
   receiving, using one or more electrodes in contact with a patient, an electrocardiogram (ECG) recording of the patient during a nominally normal sinus rhythm, wherein the ECG recording is recorded over a first time interval of 10 minutes or less;
   generating a first neural network input, the first neural network input representing the ECG recording of the patient;
   generating, using a neural network operating on a processor, an atrial fibrillation prediction for the patient as a function of the first neural network input, wherein the neural network is trained by:
      receiving current parameter values of the neural network;
      receiving one or more training examples comprising normal sinus rhythm ECGS correlated to labels indicating target atrial fibrillation predictions, wherein the target atrial fibrillation predictions comprise known and validated atrial fibrillation experienced by patients at another time;
      comparing atrial fibrillation predictions of the neural network to the target atrial fibrillation predictions; and
      updating the current parameter values of the neural network as a function of the comparison; and
   displaying, on a display device communicatively connected to the processor, the atrial fibrillation prediction for the patient.

2. The method of claim 1, wherein the neural network generates the atrial fibrillation prediction for the patient based on features of the nominally normal sinus rhythm as indicated by the ECG recording.

3. The method of claim 1, wherein the first time interval is less than or equal to thirty seconds, fifteen seconds, ten seconds, or five seconds.

4. The method of claim 1, wherein the first time interval is less than or equal to five minutes, one minute, or forty-five seconds.

5. The method of claim 1, wherein the patient is a human.

6. The method of claim 1, wherein the neural network comprises at least one of a feedforward portion, a convolutional portion, a recurrent portion, or a capsule portion.

7. The method of claim 1, wherein the ECG recording of the patient comprises a 12-lead ECG recording.

8. The method of claim 1, wherein the ECG recording of the patient comprises a single-lead ECG recording.

9. The method of claim 1, wherein the ECG recording of the patient is based on fewer than twelve leads.

10. The method of claim 1, wherein the atrial fibrillation prediction indicates a likelihood of the patient experiencing atrial fibrillation.

11. The method of claim 1, wherein the atrial fibrillation prediction indicates a selection of one of a plurality of possible monitoring or treatment plans.

12. The method of claim 11, wherein the plurality of possible monitoring or treatment plans include a first plan to administer anticoagulants to the patient, a second plan to not administer anticoagulants, and a third plan to administer a continuous ECG for further monitoring.

13. The method of claim 1, wherein the atrial fibrillation prediction indicates at least a threshold likelihood of the patient experiencing atrial fibrillation, and the method further comprises administering a treatment to lower a risk of stroke in the patient in response to identifying that the atrial fibrillation prediction indicates at least the threshold likelihood of the patient experiencing atrial fibrillation.

14. The method of claim 13, wherein administering the treatment comprises administering an anticoagulant to the patient.

15. The method of claim 1, further comprising:
   obtaining data describing a non-ECG profile for the patient;
   generating one or more second neural network inputs representing the non-ECG profile for the patient; and processing the first neural network input along with the one or more second neural network inputs with the neural network to generate the atrial fibrillation prediction for the patient.

16. The method of claim 1, further comprising:

determining one or more morphological features of the ECG recording of the patient;

generating one or more second neural network inputs representing the one or more morphological features of the ECG recording; and processing the first neural network input along with the one or more second neural network inputs with the neural network to generate the atrial fibrillation prediction for the patient.

17. The method of claim 1, wherein the method further comprises:

obtaining a second neural network input, the second neural network input representing a second ECG recording of the patient over a second time interval, the first time interval and the second time interval separated by a third time interval; and processing the first neural network input along with the second neural network input with the neural network to generate the atrial fibrillation prediction for the patient.

18. The method of claim 17, wherein the third time interval is at least a minute, an hour, a day, a week, or a month.

19. The method of claim 17, wherein the neural network further processes, along with the first neural network input and the second neural network input, a third neural network input that indicates a length of the third time interval, wherein the length of the third time interval is between a length of the first time interval and a length of the second time interval.

20. A system, comprising:

one or more electrodes configured to be in contact with a patient, wherein the one or more electrodes are configured to receive an electrocardiogram (ECG) recording of a patient, wherein the ECG recording is recorded over a first time interval of 10 minutes or less;

an interface configured to generate the ECG recording of the patient, and generate a first neural network input representing the ECG recording;

a data processing apparatus connected to the interface and configured to generate an atrial fibrillation prediction using a neural network and the first neural network input, wherein the neural network is trained by:

receiving current parameter values of the neural network;

receiving one or more training examples comprising normal sinus rhythms correlated to labels indicating target atrial fibrillation predictions;

comparing atrial fibrillation predictions of the neural network to the target atrial fibrillation predictions; and updating the current parameter values of the neural network as a function of the target atrial fibrillation predictions; and a display device connected to the interface and configured to display the atrial fibrillation prediction for the patient.

* * * * *